United States Patent
Munier et al.

(10) Patent No.: US 6,337,896 B1
(45) Date of Patent: Jan. 8, 2002

(54) METHOD FOR ACQUIRING MEASUREMENTS AND SCANNER IMPLEMENTING SAID METHOD

(75) Inventors: Bernard Munier, Seyssinet-Pariset; Guy Roziere, Voreppe, both of (FR)

(73) Assignee: Thomson Tubes Electroniques, Meudon la Foret (FR)

(*) Notice: Subject to any disclaimer, the term of this patent is extended or adjusted under 35 U.S.C. 154(b) by 0 days.

(21) Appl. No.: 09/623,523

(22) PCT Filed: Apr. 2, 1999

(86) PCT No.: PCT/FR99/00776

§ 371 Date: Oct. 3, 2000

§ 102(e) Date: Oct. 3, 2000

(87) PCT Pub. No.: WO99/51146

PCT Pub. Date: Oct. 14, 1999

(30) Foreign Application Priority Data

Apr. 3, 1998 (FR) .......................................... 98 04180

(51) Int. Cl.[7] .................................................. A61B 6/03
(52) U.S. Cl. ............................. 378/17; 378/4; 378/901
(58) Field of Search .............................. 378/4, 15, 17, 378/901

(56) References Cited

U.S. PATENT DOCUMENTS

| | | | |
|---|---|---|---|
| 4,694,399 A | * | 9/1987 | Tan et al. ..................... 378/11 |
| 4,933,562 A | | 6/1990 | Roziere |
| 5,120,950 A | | 6/1992 | Roziere et al. |

OTHER PUBLICATIONS

U.S. application No. 09/623522, filed Oct. 3, 2000, pending.

U.S. application No. 09/869,117, filed Jun. 25, 2001, pending.

* cited by examiner

Primary Examiner—David V. Bruce
(74) Attorney, Agent, or Firm—Oblon, Spivak, McClelland, Maier & Neustadt, P.C.

(57) ABSTRACT

In order to solve an analogue/digital conversion dynamic swing problem encountered with detectors, especially solid-state detectors, of a tomodensitometer, there is provision to operate converters at a greater frequency, that is to say more often. In doing this, the converters used need not have as large a conversion dynamic swing. It is shown that instead of a 20-bit conversion, one can make do with a 14-bit conversion. The various conversions are added together to construct the signal. The measurement is thereafter switched, by way of improvement, as a function of the level of the signal received. This measurement is performed according to one mode of use or another, in which modes this acceleration of the rate of analogue/digital conversion is or is not effected.

11 Claims, 4 Drawing Sheets

METHOD FOR ACQUIRING MEASUREMENTS AND SCANNER IMPLEMENTING SAID METHOD

BACKGROUND OF THE INVENTION

1. Field of the Invention

The invention relates to a process for acquiring measurements with an X-ray tomodensitometer, and a tomodensitometer for implementing the process. These apparatuses generally use a single source of X-rays and a multi-element detector opposite the source. The source and detector assembly can revolve and or move in translation relative to the body of a patient who is placed between the source and the detector.

2. Discussion of the Background

In general, the X-ray detector includes a multiplicity of individual detection elements juxtaposed so as to cover the whole of a circular arc illuminated by the X-ray source. There are nevertheless detectors which are not curved. The most well known detectors are gas-based detectors and solid-state detectors. The signals output by the detector elements are gathered periodically, digitized and transmitted to a computer in tandem with the rotation, and or with the translation of the apparatus, so as to be processed by digital computation in order to reconstruct an internal image of a slice of the body exposed to the X-rays.

For greater image resolution, it is desirable to have a large number of detection elements juxtaposed along a circular arc, or more generally along a line situated in a plane substantially perpendicular to the axis of rotation translation. Moreover, the detector can be constructed in the form of several detection assemblies juxtaposed in a direction parallel to the axis of rotation translation. In this case, the individual detection elements can be arranged as several strips of two or more elements. These elements are aligned in a direction parallel to the axis of rotation, the strips being juxtaposed along the circular arc. This makes it possible in particular to simultaneously explore two or more very fine juxtaposed slices of the body examined, since the source, by revolving, simultaneously exposes two or more adjacent series of detectors of small dimension. Such an apparatus is for example described in the document U.S. Pat. No. 5,592,523.

By way of example, a tomodensitometer can use as detection elements up to several thousand photodiodes, of the polarized type or of the photovoltaic type, individually covered by a scintillator crystal, and this number could even increase to several tens of thousands. The example which will be studied here will include around 25,000 detection elements. This results in difficulties with regard to gathering the electrical signals emanating from these numerous detection elements. The aim of the invention is to propose a mode of operation allowing the best possible solution of the technical constraints resulting from the presence of this large number of detection elements.

Among these constraints, there are:

the necessity to read the signals from all the detection elements over a very short duration, for example of the order of 0.5 milliseconds. This is because a tomodensitometer revolves continuously at a speed, for example conventional, of two revolutions per second. In a preferred example, one wishes to perform around 1000 views of the body for each revolution. A view corresponds to a given duration in the course of which the body is exposed to X-ray radiation, in a continuous or pulsed manner. The image of the view revealed on the detector corresponds to the phenomenon of radiological absorption which occurs for the duration of the view. One distinguishes the image from the view itself (portrayed directly in projection mode by the detector), and the reconstructed image of a body section in which this view participates in the reconstruction calculations. For the duration of a view, the tomodensitometer is regarded as occupying a fixed position relative to the body when processing the image. Of course, this is not true since the tomodensitometer is moving continuously. A view is nevertheless thus associated with an angle of incidence, a position: the tagging of the mean angle at which a principal axis of X-ray radiation irradiates the body. If the duration of measurement, the duration of view, were greater the final resolution of the image would not be acceptable: it would then be necessary either to take fewer views, or rotate the tomodensitometer less quickly;

the necessity to read signals over a very large dynamic swing, for example of the order of 20 bits, since the dark parts of the image yield an extremely weak signal relative to the lighter parts, and this weak signal must however be measured with some resolution (a few bits). Thus, in order to measure both 1,000,000 X-ray photons received in nominal mode, or 4 X-ray photons received at minimum, a measurement dynamic swing of 20 bits would be necessary. However, if the overall dynamic swing of the image thus represents 20 bits, the useful local dynamic swing is less demanding. This is because this useful local dynamic swing is equal to the signal-to-noise ratio. In actual fact, the signal-to-noise ratio is equal to around 1000 maximum. It is in fact equal to the square root of the number of X-ray photons received owing to the quantum phenomenon of absorption of X-rays in the body and their conversion in a scintillator. This means that out of the 20 bits measured, only 14 bits are significant. The digitizing of the measurements over such a dynamic swing nevertheless involves the adoption of circuits which are overdimensioned in terms of performance and occupy too much room in an integrated circuit;

in a solid-state detector, the necessity to process quantities of charge which may be fairly high when the detector receives large fluxes of X-ray radiation. Nominal charges of the order of 100 picocoulombs, pC, per photo diode are in fact encountered. Such charges require large storage areas. This, however, poses size problems with regard to achieving the required capacities for storing these charges, given the low operating voltages of these integrated circuits. By way of example, the detectors can be diodes of the reverse-bias type, a capacitor being fashioned at the terminals of a diode owing to its reverse bias. A preamplifier can be connected successively to each of these diodes so as to recharge the capacitor with the charges which it lost under the action of the light received by the diode. The quantity of charge reinjected by the preamplifier forms the measurement signal. Preferably, for linearity reasons, non-biased diodes, of the photovoltaic type, will be used. They produce a DC current proportional to the illumination which they receive. The measurement of the X-ray radiation is effected therein via a link from this photovoltaic diode to an integrator, and via the integration over a small duration of this current signal. At each new duration the integrator is previously reset to zero. In this latter case the integrator is the facility for storing the charges to be measured whereas in the previous case it is the reverse-fashioned capacitor.

SUMMARY OF THE INVENTION

To allow the construction of an apparatus complying with these constraints without involving a prohibitive manufacturing cost, the present invention proposes a process for obtaining tomographic images, preferably using at least one array of elementary detectors, a charge storage element associated with each detector, and a circuit, a multiplexer, associated with the array of storage elements so as to periodically instruct the connecting of the various detectors to their storage elements. The successive analogue signals output by the multiplexer are transformed into digital signals downstream by an analogue/digital converter.

The principle of the invention then consists, in the course of a view, in splitting up the signal integration time so as to reduce the quantity of charge to be measured. Indeed, under these conditions the detector facility used need no longer be capable of accumulating large quantities of charge. Moreover, the analogue/digital converter no longer needs such a large dynamic swing. It can be shown that one thus goes from 20 bits to 14 bits. Because samplings and multiple quantizations are then effected during a view, it is then of course necessary to execute a summation of the quantization results so as to produce a signal corresponding to the view, for each detector.

However, the sought-after result is attained even so, namely:

the capacity required for the storage elements is reduced by a factor n (n being a measurements acceleration factor), the frequency of the analogue/digital converter is increased by the factor n, the dynamic swing of this analogue/digital converter is, overall, reduced in a factor lying between n and root n.

The subject of the invention is therefore a process for acquiring measurements with a tomodensitometer comprising the following steps:

a body is irradiated, during a given view, with X-ray radiation, an analogue signal is measured for this view, in each detector of an array of detectors, this signal representing the effect of the absorption of the X-ray radiation in the body at the location of each of these detectors, each analogue detector signal is sampled and converted into a digital detector signal, characterized in that the analogue signal from each detector is sampled with n repetitions in the course of the view, and the n converted signals from each detector are added together to construct the digital view signal of each detector.

Its subject is also a tomodensitometer furnished with a device for acquiring measurements comprising an X-ray tube for irradiating a body with X-ray radiation during successive views, an array of detectors for measuring an analogue signal representing the effect of the absorption of the X-ray radiation in the body at the location of each of these detectors during a view, an analogue/digital converter for sampling and converting each analogue detector signal into a digital detector signal, a sequencer for driving the array of detectors and the converter at the rate of the views, characterized in that it includes means in the sequencer for driving the array of detectors and the converter at a rate n times greater than the rate of the views and, an adder for adding together the n converted signals from each detector so as to construct the digital view signal of each detector.

Another problem to be solved with such tomodensitometers is related to the number of their detectors, which as stated hereinabove may be very large. The assembly of control circuits of all these detectors then constitutes a very voluminous system to be constructed, even when employing the most modern miniaturization techniques. It is not in reality easy to go from manufacturing a detector with 700 detection elements to a detector with 25,000 detection elements.

To solve this other problem, according to another characteristic of the invention, groupings of detectors are constructed and common processing is applied to all the detectors of these groups. The invention starts in fact from the following principles which it has highlighted. Firstly, in a projection-mode image, the change in contrast is never abrupt, even if the dynamic swing of measurement over the entire image is itself large. This is because the organs of the body of a patient either interpenetrate or are viewed in projection through other organs. Therefore, there is always a transition zone between the images of these organs. This transition zone is relatively large on the scale of the size of the detectors. For this transition zone, the contrast may then be regarded as not changing excessively.

Secondly, and by way of adjunct, because of the slow rotation of the tomodensitometer, one may regard the absorption phenomenon measured in a detector, at the moment of a view, as being the same phenomenon (with the same dynamic swing) as the phenomenon which occurs in a neighbouring detector at a following view.

Stated otherwise, in the invention, it has then been considered that it was already possible to group the detectors of a region. The effect of this grouping is to subject the detectors of a group to one and the same mode of measurement. In practice, these considerations have led to the construction of groups of detectors for which the measurement dynamic swing may be regarded as lying within the same range. According to the invention, each group of detectors is then allocated a measurement range. This leads to the simplifying of the electronic detection circuits. The range is determined by ensuring that the greatest measurement performed for a detector of a group lies within the smallest possible measurement range assigned to this group. By way of improvement, the determination is performed during a view, and the assignment is carried out at the following view.

BRIEF DESCRIPTION OF THE DRAWINGS

The invention will be better understood on reading the description which follows and on examining the figures which accompany it. The latter are given merely by way of wholly non-limiting indication of the invention. The figures show.

DESCRIPTION OF THE PREFERRED EMBODIMENTS

Figure 1:
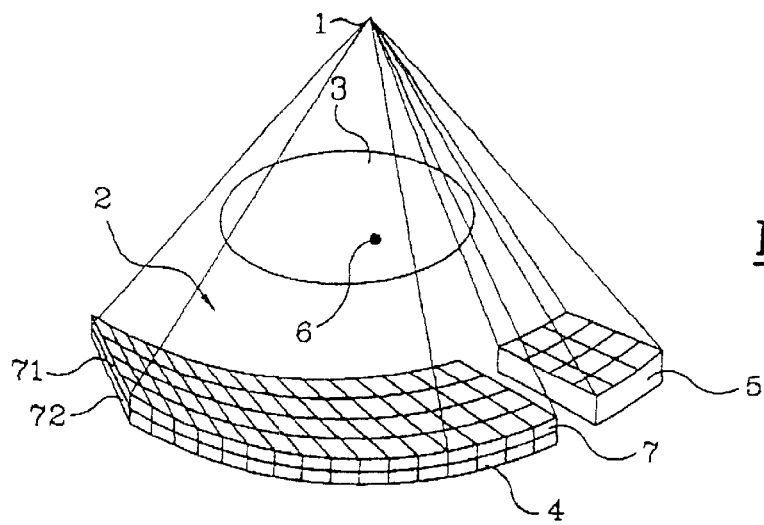
FIG. 1: the diagrammatic representation of the essential means of a tomodensitometer.

FIG. 1 shows the essential elements of a tomodensitometer. This tomodensitometer is useable in the framework of the invention. This tomodensitometer includes a source 1 producing X-ray radiation 2 which irradiates a body 3 interposed between the source 1 and a detector 4. The detector 4 can furthermore include an auxiliary detector 5 situated outside the X-ray field masked by the body 3. The auxiliary detector 5 can serve to normalize the measurements performed. The tomodensitometer revolves about an axis of rotation whose trace 6 is visible. The detector 4 is a detector including a multiplicity of detection elements 7.

The detector 4 includes a layer 71 of scintillator elements superimposed on a layer 72 of detection elements proper. The scintillator elements of the layer 71 perform a conversion of the X-rays into light rays to which the photodetector elements of the subjacent detection layer 72 are sensitive.

According to the sensitivity allowed at present, for one X-ray photon received in the layer 71, around 1000 light photons are produced by a scintillator crystal element. The scintillator crystal elements are separated from one another by transition walls between one crystal and another.

Figure 2:
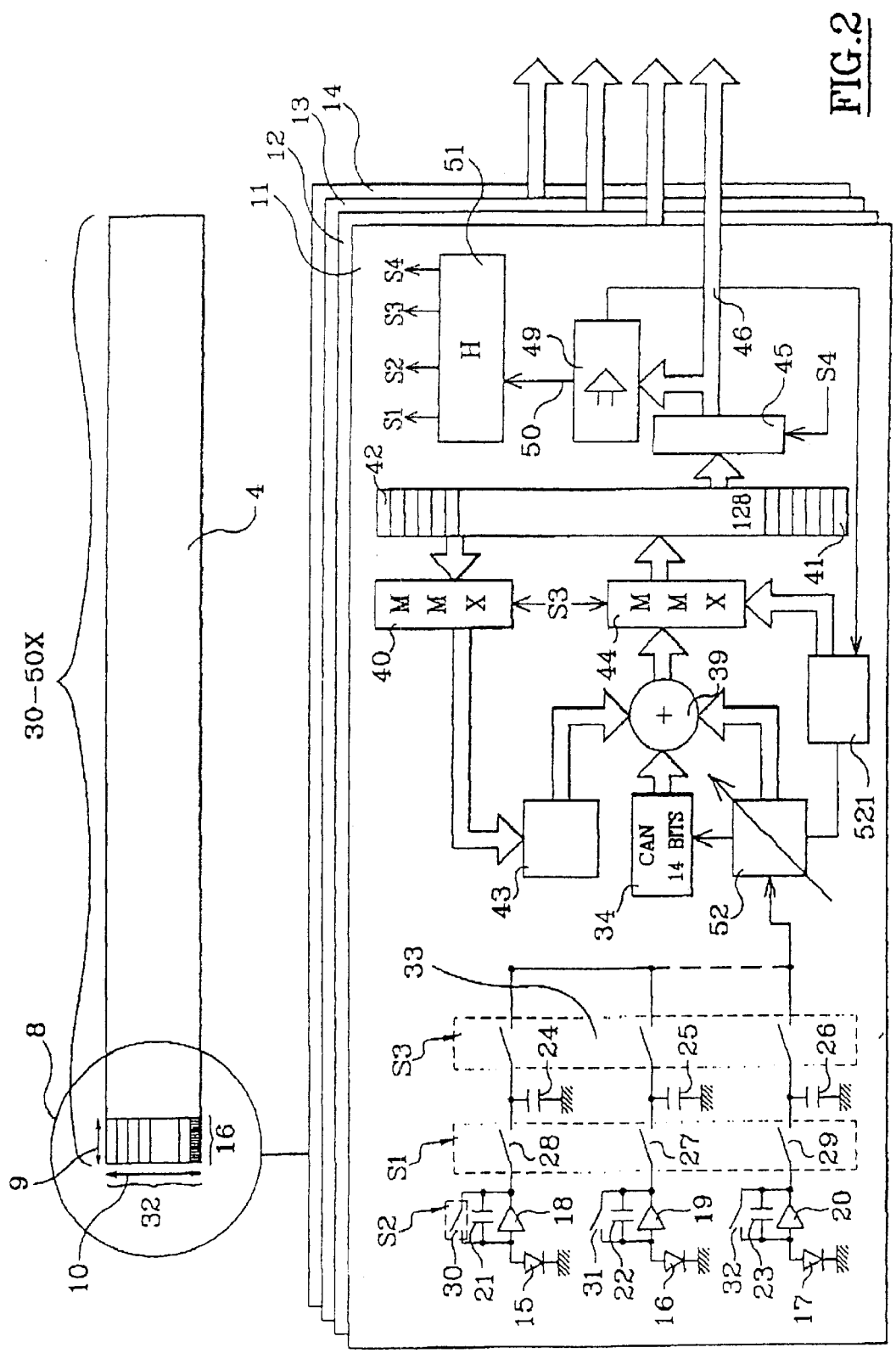
FIG. 2: a representation of the modification of the detection circuit of a tomodensitometer so as to enable it to implement the process of the invention.

FIG. 2 shows an exemplary embodiment of the detection elements of the detector 4. This detector 4 includes an assembly of modules 8. The modules 8 are matrices of detection elements. The modules 8 are placed side by side in the direction of the length of the detector 4. In one example, the length 9 of a module is of the order of 20 mm. In the same example, there may be between 30 and 50 modules aligned in the direction of the length of the detector 4. This results in a detector length of between 60 cm and 1 metre. In this same example, the width 10 of the module 8, in the part thereof useful for detection, is of the order of 64 mm. This therefore makes it possible to acquire sections situated within a thickness of the order of 40 mm inside the interposed body 3. The purpose of the numerical examples given hereinbelow is merely to simplify the explanation and they cannot lead to a limiting of the scope of the protection obtained by the invention. In this example, the modules include an arrangement of 32 rows, stacked one above the other in the direction of the width 10, and 16 columns placed side by side in the direction of the length 9 of the detector 4. Therefore, the module 8 includes 512 elementary detectors. To fix matters, it will be presumed moreover that the tomodensitometer revolves at a speed of two revolutions per second and that one wishes to perform 1000 views over each revolution. The duration of a view is therefore 500 microseconds. In the course of each of the views, in the course of each of these 500 microseconds, it is appropriate to measure for all the modules, and for all the elementary detectors in each module, the illumination signal detected.

The bottom of FIG. 2 shows the architecture of the embodiment of the detectors of a module 8. Each module of detectors preferably consists of four subgroups 11 to 14 of elementary detectors and of associated processing circuits. The subgroup 11 thus includes 128 detectors denoted 15 to 17. In this example, these detectors are diodes of the photovoltaic type. The subgroups include for example detectors situated in 8 adjacent columns out of 16 and in 16 rows out of 32. As a variant, two subgroups per module are constructed.

The photodiodes 15 to 17 are detection elements installed in the layer 72 of photodetector elements of the detector 4. They receive luminous radiation corresponding to the X-ray radiation received at the location of the scintillator crystal which surmounts them. These diodes are linked by their two terminals, on the one hand, in common to earth, and on the other hand, in an individualized manner, each to the input of an amplifier 18 to 20 respectively. The amplifiers 18 to 20 are operational type amplifiers. In one example, they can consist of a simple transistor. The amplifiers 18 to 20 are mounted as integrators by way of capacitors 21 to 23 respectively which loop their outputs back to their inputs. The outputs of the amplifiers 18 to 20 are furthermore linked to storage capacitors 24 to 26 respectively. The link between the outputs of the amplifiers 18 to 20 and the capacitors 24 to 26 is constructed by way of switches 27 to 29 controlled by a signal S1.

When the switches 27 to 29 are closed, the amplifiers 18 to 20 charge the capacitors 24 to 26 instantaneously. The charge injected into the capacitors is dependent on the voltage which the integrators 18 to 20 have reached on termination of an integration duration (corresponding to a view, hence corresponding to 500 microseconds in practice).

When the voltage available at the outputs of the amplifiers 18 to 20 has been transmitted to the capacitors 24 to 26, the amplifiers 18 to 20 are reinitialized by a signal S2 applied to a gang of switches 30 to 32 respectively, shunted to the capacitors 21 to 23. The reinitialization is instantaneous. On termination of the signal S2, the diodes 15 to 17 recommence injecting current into the amplifiers 18 to 20.

A multiplexer 33 makes it possible to link, each in turn, the storage capacitors 24 to 26 to an analogue/digital converter 34 which, in a preferred example of the invention, is a 14-bit analogue/digital converter.

Figure 3A:
FIGS. 3a to 3g: time charts of signals implemented respectively in the state of the art and in the invention, and corresponding to the process.
Figure 3B:
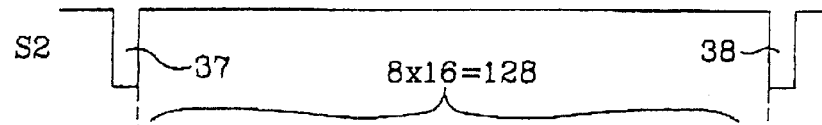
Figure 3C:
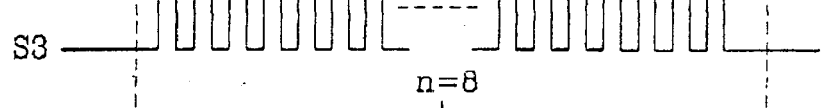

In the state of the art represented by FIGS. 3a to 3c which show the synchronizations of the signals S1 to S3, the signal delivered by the converter 34 was a signal relating to a view. It was also distinct for each of the detectors 15 to 17. FIG. 3c shows in particular that a signal S3 which includes 8×16=128 pulses made it possible, in the course of a view, to sample, each in turn, and to digitize the signals contained in the 128 capacitors 24 to 26. With the four subgroups 11 to 14 one therefore had the 4×128=512 measurements corresponding to a module, for each view. The duration of the view is here the duration which separates the pulses 35 and 36 of the signal S1, or 37 and 38 of the signal S2 in FIGS. 3a and 3b.

It will be observed that, in the module including 512 elementary detectors, there are 4 converters 34 per module 8. There is one for each of the subgroups 11 to 14. Given the number of modules, 50, there are 200 converters 34 in the device of the invention. Moreover, these converters are simple.

Given the large dynamic swing of the signal to be measured, and the likewise large number of converters 34, it was appropriate, according to the invention, to advocate converters 34 of smaller size (14-bit) rather than converters according to the state of the art (20-bit). In the invention, to solve this problem, it was decided to increase the frequency with which the converters 34 sample then digitize the contents of the capacitors 24 to 26.

Figure 3D:
Figure 3E:
Figure 3F:
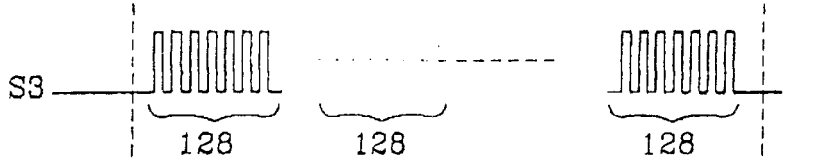

Correspondingly, the frequency of transfer of the output voltages from the amplifiers 18 to 20 to the capacitors 24 to 26 is increased in the same way. This is shown in FIGS. 3d to 3f corresponding to FIGS. 3a to 3c respectively. It is seen that in these groups of figures, the duration D of a view remains the same. In one example, it is still 500 microseconds. On the other hand, in the invention, the integration, sampling and quantization are executed n times during this period. In a preferred example, n=8. The significance of the signal S3 of FIG. 3f is that the converter 34 delivers the 128 results, n times more frequently than in the framework of FIG. 3c.

In the invention, furthermore, as and when the results are delivered by the converter 34 in respect of a detector, they are added in an adder 39 to results corresponding to the same detector and delivered by this same converter, but at a previous quantization. For this purpose, a first multiplexer 40 which also runs at the rate of the signal S3, taps off from a memory 41, at an address 42 (changing at the rate of the signal S3), the result of a previous quantization which had been stored there. This result is stored in a buffer memory 43. The buffer memory 43 is tied up with the adder 39. At the due moment, the adder 39 correspondingly adds the content of the memory 43 to the result delivered by the converter 34. The output of the adder 39 is linked to a second multiplexer 44 whose role is to store, again at the address 42, the result of the addition of the old content of the address 42 with the quantization result delivered by the converter 34.

Figure 3G:

FIG. 3g shows a supplementary signal: the signal S4. The signal S4 is the signal synchronous to the signal S1 or to the signal S2 of the state of the art, FIGS. 3a and 3b. The signal S4 controls a third multiplexer 45 which rapidly extracts from the memory 41 the 128 data which were stored there. The memory 41 includes memory cells preferably of 20 bits. The reading of the memory 41 by the multiplexer 45 must be fast. This is because it must occur during the first of the n quantizations carried out by the analogue/digital converter 34 in the course of the view.

If need be, the multiplexer 45 is combined with the multiplexer 40, the signal being available on the output 46 only once every n times.

Figure 4:
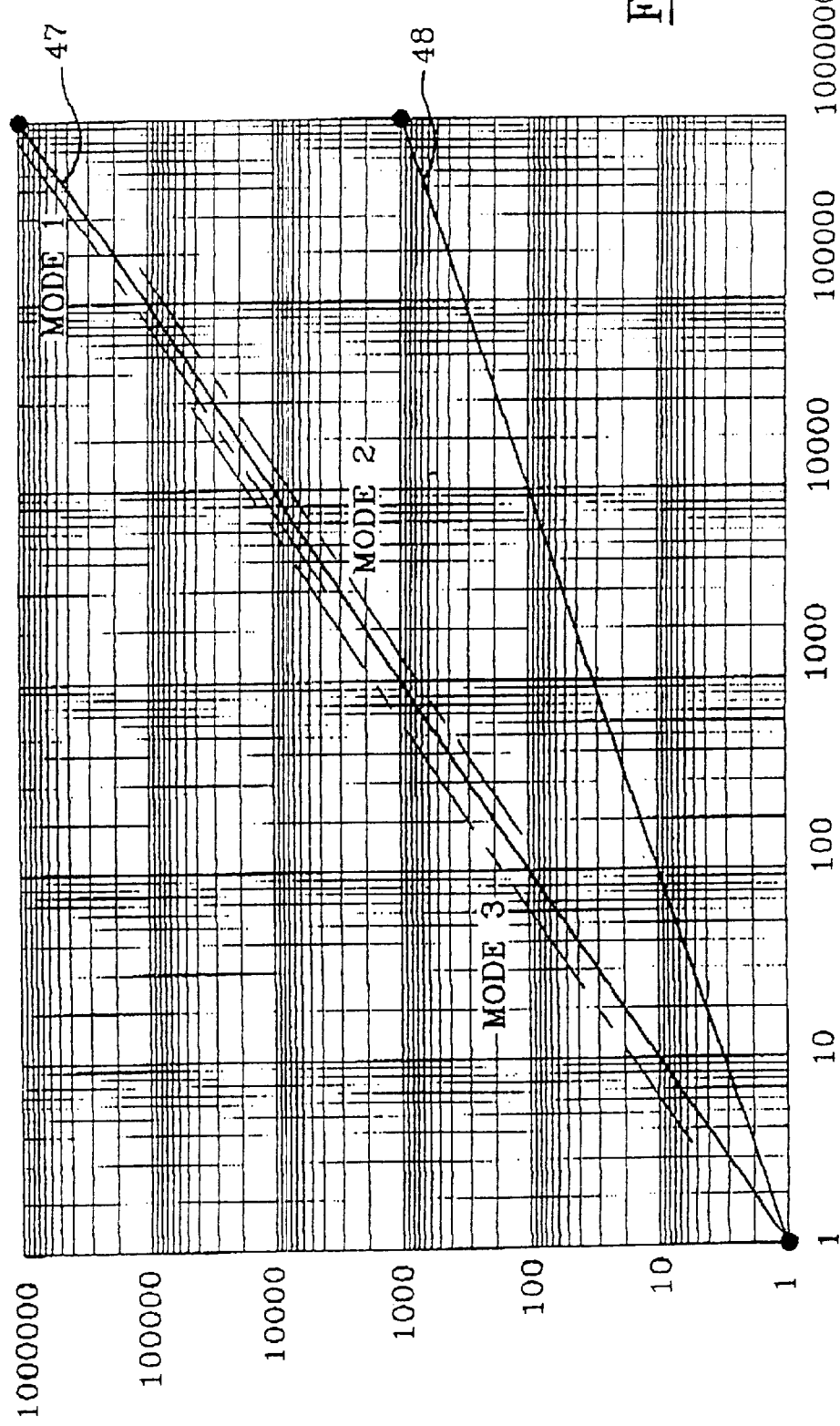
FIG. 4: a chart showing various modes of use of the process of the invention as a function of the value of the signals detected.

FIG. 4 shows various modes of use of the tomodensitometer of the invention and of its detection system. The abscissa gives the number of X-ray photons incident over the duration of a view (500 microseconds) on an elementary detector of the detector 4. The ordinate shows the output signal expected after digitization. The scales of the co-ordinate axes are logarithmic so as to take into account a 20-bit large overall dynamic swing. The straight line 47 shows the (normal) processing performed by the detection chain with a one-for-one conversion rate. The straight line 48 also shows the change in the signal-to-noise ratio resulting from the quantum detection by the scintillator crystals. In particular, for nominal illumination, the signal-to-noise ratio is equal to 1000 (square root of 1 million).

Depicted on the chart of FIG. 4 are three domains entitled Mode 1, Mode 2 and Mode 3 respectively and corresponding to different spans of X-ray illuminations. For Mode 1, the signal detected corresponds to charges lying between 12.5 pC and 100 pC. According to the invention, for signals corresponding to this mode, one uses an acceleration of the rate of tapping off of the output voltages from the amplifiers 18, 19 and 20 as well as the corresponding quantization by the converter 34. Specifically, in this case, the converters 34 will operate at the rate of the signal S3 of FIG. 3f. In the case where n=8, the result stored in the cell 42 of the memory 41 will equal, on termination of the view, a signal coded on 17 bits (14+3) positioned in the high-order bits. This is because the addition of eight signals coded on 14 bits leads to a result on 17 bits. The adder 39 is therefore a 17-bit adder.

According to the improvement to the invention, a signal corresponding to each elementary detector of a subgroup 11 of elementary detectors is measured in a comparator 49 linked to the output 46 of the multiplexer 45. If the signal from at least one of these elementary detectors is above, equivalently, 12.5 pC, accelerated acquisition is used for all the elementary detectors of this subgroup. On the other hand, if the signal from all the detectors of a subgroup is below 12.5 pC, one decides no longer to employ the improvement to the invention. For this purpose, the comparator 49 delivers a signal 50 whose role is to transform the signal S1 visible in FIG. 3d into a signal S1 visible in FIG. 3a. In practice, the frequencies of the signals S1, S2 and S3 are then divided by n. A clock 51, playing a sequencer role, therefore delivers, as a function of the signal 50, signals S1, S2, S3 which may or may not be accelerated. It is easy, with a cyclic counter driven by a very fast clock, to investigate one bit of the signal delivered by this counter and to construct the pulses S1 to S3 with the state of this bit. For an eightfold acceleration, it is sufficient to investigate one lower-order bit, to shift by three units.

Preferably, the acceleration is no longer effected when the signal detected is weak and should the analogue/digital converter's digitization noise be greater than the X-ray quantization noise due to the scintillator crystal.

It has been observed moreover that the gradient of the absorption varies little in the image. In practice, the gradient is below 50 or 100. This signifies that the signal detected on the detectors of a module 8 is not too different from the signal detected on the detectors of an adjacent module. This has led to the groups of detectors being constructed according to the invention.

Furthermore, given the slow rotation of the tomodensitometer, the zones of the body which are viewed by adjacent detectors in the module 8, in the course of a view, are viewed almost by the same detectors of the module 8 at the following view. Thus one is able to predict on one view what will be the signal on a following view, since locally the signal will moreover vary little, the contrast having no abrupt changes. This then makes it possible, by way of improvement, when making a measurement for a view, to decide to apply the signal 50, not in the course of the view, but for a following view. Stated otherwise, the signal 50 which causes the toggling from Mode 1 to Mode 2, or vice versa, is applied to the clock 51 only after the pulse of the signal S4 which marks the end of the current view.

In certain cases, the signal detected is much weaker than an equivalent at 1.6 pC. In this case, in order to use the converter 34 to the maximum of its range, the signal originating from the storage elements 24 to 26 is amplified beforehand with an amplifier 52, before conversion. This amplification is preferably performed if all the detector signals of a group are below a threshold. For example, the amplification will be in a ratio 8. Stated otherwise, with such an amplification the dynamic swing of the converter 34 is fully used. However, owing to the amplification carried out, it is then appropriate to shift, in the cells 42 of the memory 41, the result towards the low-order bits. If the amplification factor equals 8, the result has to be shifted by 3 bits in the low-order direction. In reality, the amplification factor will not be 8. Consequently, the result of the conversion will be divided by the actual amplification factor. This will be carried out by a circuit interposed between the converter 34 and the adder 39.

It will be noted that the thresholds of 12.5 pC and 1.6 pC are arbitrary, although fairly well suited to the problem.

The signal from the comparator 49 which controls the amplifier 52 is moreover stored in a selection circuit 521. The circuit 521 is then tied up with the multiplexer 44 so as to bring about, at the moment of recording in memory 41, a recording which may or may not be shifted by 3 bits towards the low-order bits.

Specifically, one will thus have obtained a dynamic swing of 14+3+3=20 bits by only ever using an analogue/digital converter capable of a 14-bit dynamic swing.

If need be, the amplification by the amplifier 52 and the acceleration of the rate can be combined.

Figure 5:
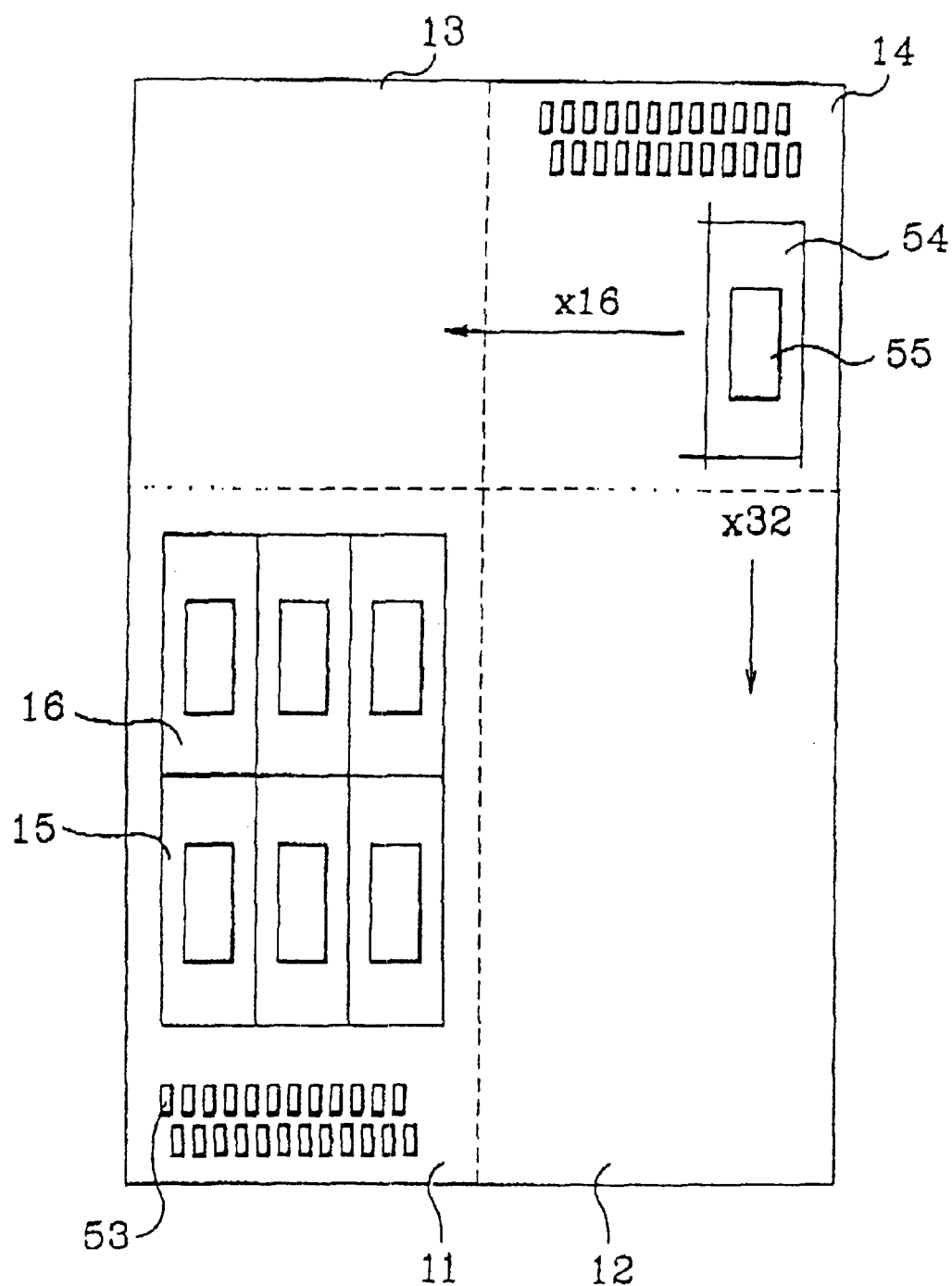
FIG. 5: a diagrammatic representation of the embodiment of a detection module used in the invention.

FIG. 5 shows a practical exemplary embodiment of a module in the case where the detector includes photodiodes of photovoltaic type. FIG. 5 shows a module 8 including 512 elementary detectors distributed into 32 rows and 16 columns. FIG. 5 shows the 4 subgroups 11, 12, 13 and 14, each including 128 photodetectors. In one example, these photodetectors forming the layer 72 are made on a silicon substrate carried by a ceramic support which will moreover carry the control circuits. Metallizations such as 53 are each linked by connections (not represented) to an individualized photodetector. The other terminal of these photodetectors is linked to earth, a metallization (not represented) subjacent to the substrate and common to all.

In one example, the photodetectors correspond to an area of 0.6 mm times 1.2 mm, smaller than the dimensions of 1.25 mm times 2 mm given previously. There is therefore a neutralized frame around each detecting zone 55. The purpose of this neutralized frame is to electrically insulate the photodetectors from one another and furthermore to adapt to the size of the scintillator crystals deposited on a photodetector. There is not actually any drawback in acting in this manner since the quantum detection phenomenon occurs in a scintillator crystal of the layer 71 which surmounts the detector 55 and the frame 54. The photo diode 15 is for its part sensitive to illuminous radiation containing, approximately, 1000 times more photons. In this case, the useful areas of the diodes are smaller than the corresponding area presented by a scintillator crystal which surmounts them.

What is claimed is:

1. Process for acquiring measurements with a tomodensitometer which includes a source of X-rays intended to irradiate a body, during a given view in which:

an analogue signal is measured for this view, in each detector of an array of detectors, this signal representing the effect of the absorption of the X-ray radiation in the body at the location of each of these detectors, each analogue detector signal is sampled and converted into a digital detector signal, characterized in that the analogue signal from each detector is sampled with n repetitions in the course of the view, and the n converted signals from each detector are added together to construct the digital view signal of each detector.

2. Process according to claim 1, characterized in that groups of detectors are constructed the signal from at least one detector of a group is compared with a threshold, and the signals from the detectors of the group are sampled with n repetitions if this signal from at least one detector of the group is above this threshold.

3. Process according to claim 1, characterized in that groups of detectors are constructed, the signals from all the detectors of a group are compared with a threshold, and the signals from the detectors of the group are amplified before conversion if each of these signals is below a threshold.

4. Process according to claim 2 characterized in that analogue signals from detectors which correspond to a view subsequent to that during which the comparison is made are sampled with n repetitions or are amplified.

5. Process according to claims 1, characterized in that the detectors are photovoltaic diodes and in that in order to make measurements there is integrated in an integrator, in the guise of detector signal, a current signal produced by each photovoltaic diode over a duration n times smaller than the duration of a view before sampling this detector signal, and the integrator is reset to zero before a new integration of this current.

6. Tomodensitometer furnished with a device for acquiring measurements comprising an X-ray tube for irradiating a body with X-ray radiation during successive views, an array of detectors for measuring an analogue signal representing the effect of the absorption of the X-ray radiation in the body at the location of each of these detectors during a view, an analogue/digital converter for sampling and converting each analogue detector signal into a digital detector signal, a sequencer for driving the array of detectors and the converter at the rate of the views, characterized in that it includes means in the sequencer for driving the array of detectors and the converter at a rate n times greater than the rate of the views and, an adder for adding together the n converted signals from each detector so as to construct the digital view signal of each detector.

7. Tomodensitometer according to claim 6, characterized in that it includes groups of detectors, a comparator assigned to a group so as to compare a signal from at least one detector of a group with a threshold, and a circuit for controlling the driving at a rate n times greater if this signal from at least one detector of the group is above this threshold.

8. Tomodensitometer according to claim 6, characterized in that it includes groups of detectors, a comparator assigned to a group for comparing the signals from all the detectors of a group with a threshold, and an amplifier for amplifying before conversion the signals from the detectors of the group of these signals are below a threshold.

9. Tomodensitometer according to claim 7, characterized in that a group detectors includes two or four detector subgroups mounted with their control circuits all together on the same support, for example a ceramic support.

10. Tomodensitometer according to claim 6, characterized in that the detectors are photovoltaic diodes each associated with a controlled integrator.

11. Tomodensitometer according to claim 6, characterized in that the detectors include photo diodes whose detection area is less than the detection area of a scintillator crystal which surmounts them.

\* \* \* \* \*